(12) United States Patent
Hahn et al.

(10) Patent No.: US 6,699,040 B1
(45) Date of Patent: Mar. 2, 2004

(54) MATERIAL FOR DIFFERENTLY MODIFYING THE OPTICAL PROPERTIES OF DIFFERENT CELLS

(75) Inventors: Rainer Hahn, Tübingen (DE); Klaus Irion, Liptingen (DE)

(73) Assignee: Karl Storz GmbH & Co., KG (DE)

( * ) Notice: Subject to any disclaimer, the term of this patent is extended or adjusted under 35 U.S.C. 154(b) by 0 days.

(21) Appl. No.: 09/720,232

(22) PCT Filed: Jun. 11, 1999

(86) PCT No.: PCT/EP99/03778
§ 371 (c)(1),
(2), (4) Date: May 18, 2001

(87) PCT Pub. No.: WO00/01350
PCT Pub. Date: Jan. 13, 2000

(30) Foreign Application Priority Data

Jun. 19, 1998 (DE) .......................................... 198 27 417

(51) Int. Cl.$^7$ ................................................. A61C 5/00
(52) U.S. Cl. ................................................... 433/217.1
(58) Field of Search ............................... 433/215, 217.1

(56) References Cited

U.S. PATENT DOCUMENTS

| | | | |
|---|---|---|---|
| 3,667,454 A | 6/1972 | Prince | |
| 4,685,596 A | 8/1987 | Mattheis | |
| 5,033,961 A | 7/1991 | Kandler et al. | |
| 5,098,291 A | 3/1992 | Curtis et al. | |
| 5,422,093 A | 6/1995 | Kennedy et al. | |
| 5,558,518 A | 9/1996 | Bab et al. | |
| 5,570,182 A | 10/1996 | Nathel et al. | |
| 5,620,700 A | 4/1997 | Berggren et al. | |
| 5,719,197 A | * 2/1998 | Kanios | 514/772.6 |
| 6,066,628 A | * 5/2000 | Stojiljkovic et al. | 514/185 |

FOREIGN PATENT DOCUMENTS

| | | |
|---|---|---|
| CA | 983900 | 2/1976 |
| DE | 2725793 | 6/1977 |
| DE | 8517634.6 | 10/1985 |
| DE | 68906167 | 1/1989 |
| DE | 29705934 | 4/1997 |
| EP | 0049905 | 10/1981 |
| EP | 0300277 | 7/1988 |
| EP | 0743029 | 4/1996 |
| EP | 0774235 | 8/1996 |
| JP | 92-403005 | 10/1992 |
| JP | 98-172444 | 2/1998 |
| RU | 2101047 | 1/1998 |
| WO | WO 94/17797 | 2/1993 |
| WO | WO 93/21992 | 4/1993 |
| WO | WO 95/10243 | 10/1994 |
| WO | WO 95/07077 | 3/1995 |
| WO | WO 96/39188 | 6/1996 |
| WO | WO 98/10711 | 9/1996 |
| WO | WO 98/06456 | 6/1997 |
| WO | WO 98/09155 | 8/1997 |

OTHER PUBLICATIONS

Ackermann, et al, *Simulations on the selectivity of 5–aminolaevulinic acid–induced fluorescence in vivo,* J. of Photochemistry and Photobiology, p. 121–28, vol. 47, (1998).

Peng, et al, *5–Aminolevulinic Acid–Based Photodynamic Therapy,* American Cancer Society, p. 2282–308, (Jul. 1997).

Webber, et al, *On–line fluorescence of human tissues after oral administration of 5–aminolevulini acid* J. of Photochemistry and Photobiology, p. 209–14, vol. 38, (1997).

Baumgartner, et al, *Inhalation of 5–aminolevulinic acid: a new technique for fluoresence detection of early stage lung cancer,* J. of Photochemistry and Photobiology, p. 169–74, Vol 36, (1996).

Roper, et al, *Tetrapyrrole biosyntesis in several haem–dependent anaerobic pathogens,* Reviews in in Medical Microbiology, p. S13–S17, (1997).

Messman, et al, *Photodynamic diagnosis of gastrointestinal precancerous lesions after sensitization with 5–aminolaevulinic acid: a pilot study,* Dtsch. Med. Wschr., p. 515–21, vol. 123 (Apr. 1998).

Leunig, et al, *Fluorescence Imaging and Spectroscopy of 5–Aminolevulinic Acid Induced Proto–porphyrin IX for the Dectection of Neoplastic Lesions in the Oral Cavity,* Am. J. of Surgery, p. 674–77, vol. 172 (1996).

Leunig, et al, *Fluorescence Photodetection of Neoplastic Lesions in the Oral Cavity Following Topical Application of 5–Aminolevulinic Acid,* Laryngo–Rhino–Otol., p. 459–64, vol. 75 (1996).

Grant, et al, *Photodynamic therapy of oral cancer: photsensitisation with systemic aminolaevulinic acid,* The Lancet, p. 147–48, vol. 342 (Jul. 1993).

Vonarx, et al, *Potential Efficacy of a Delta 5–Aminolevulinic Acid Bioadhesive Gel Formulation for the Photodynamic Treatment of Lesions of the Gastrointestinal Tract in Mice,* J. Pharm. Pharmacol, p. 652–56, vol. 49 (Jul. 1997).

\* cited by examiner

Primary Examiner—Todd E. Manahan
(74) Attorney, Agent, or Firm—St. Onge Steward Johnston & Reens LLC

(57) ABSTRACT

A material for modifying the optical properties of cells comprises a basic material and a modification substance distributed in the basic material at a prescribed concentration, wherein the basic material comprises a viscous fluid, a gel, a two-dimensional or three-dimensional porous substrate or a material which hardens in situ.

22 Claims, 8 Drawing Sheets

MATERIAL FOR DIFFERENTLY MODIFYING THE OPTICAL PROPERTIES OF DIFFERENT CELLS

RELATED APPLICATIONS

This application claims the benefit, under Title 35, United States Code, Section 119(a)–(d) and (f), of German Patent Application No. 198 27 417.3, filed on Jun. 19, 1998.

This application claims the benefit, under Title 35, United States Code, Section 365, of International Patent Application No. PCT/EP99/03778, filed on Jun. 1, 1999.

FIELD OF THE INVENTION

The invention relates to a material for differently modifying the optical properties of different cells, to an apparatus for the application of such a material, to a diagnostic apparatus for determining the optical properties of cells which have been exposed to such a material, and to an apparatus for irradiating cells whose optical properties have been differently modified with such a material.

BACKGROUND OF THE INVENTION

Periodontosis is a widespread disease of the attachment apparatus of the teeth. Periodontopathies are caused by bacteria located in periodontal pockets (subgingivally). Some of these are bacteria which are bound adherently to the root surface and are usually Gram-positive and calcified to give concrements (subgingival calculus), and the others are bacteria which face the soft tissue of the pocket, are non-adherent and are usually Gram-negative, and which, for example, in part are motile in the pocket fluid. It is precisely these motile bacteria which play an essential role in the progression of periodontitis.

During the progression of periodontitis, the bacteria may migrate through the pocket's epithelium and penetrate into the subepithelial connective tissue, so that they surround the inflammatory infiltrate. Complicated interactions occur with the patient's immune defenses which are massively [lacuna] at this point and which lead, via (micronegroses, purulent abscesses or as reaction to the immune interaction for example through activation of osteoclastic endogenous cells, to loss of periodontal supporting tissue and development or deepening of a periodontal pocket and/or retraction of the gingival soft tissue. Particularly important in this connection are processes which take place deep inside the pocket or in problem regions such as, for example, the root furcation.

Recommended to date for reducing microbes in the pockets are mechanical cleaning techniques (for example scaling, curettages, cleaning with ultrasonic instruments) or simple pocket irrigations. Systemic administration of antibiotics is associated with considerable side effects, firstly because of the broad spectrum of the causative bacteria, and secondly because the bacteria are located outside the blood circulation. Local administration techniques through application of the antibiotics directly into the periodontal pockets often have an unreliable effect because diffusion into all the pocket regions is inadequate or deposition does not last long enough or the level of the active substance combination is inadequate. Antibiotics are therefore normally administered only as a measure supporting conventional, usually mechanical, procedures.

Because of the complex geometries of the affected periodontia or periodontal pockets, access to the diseased tissue regions is impeded, and the desired reduction in microbes is often not achieved. The consequence is after various time intervals, depending on the patient's immunological predisposition which is usually affected, recolonization of a previously treated pocket with a recurrence of the disease. It is particularly difficult to reduce microbes in the region of the infiltrated pocket epithelium and the adjoining connective tissue.

The first requirement for improved therapy is to have more detailed information about the current status of the disease to allow a better prediction to be made about the future development of the disease, especially the occurrence of acute episodes of the disease. It is to date possible to identify a previously active pocket only subsequently on the basis of pus discharge from the pocket. If this identification is possible, however, loss of supporting tissue has already occurred. Bacterial genetic testing which has recently been employed for the diagnosis of individual bacteria in periodontal pockets is costly and requires several days for evaluation. For these reasons, it is unsuitable for routine applications. It is moreover possible to derive information only about the genomes of the bacteria from such testing. Distinction according to the metabolic activities of the bacteria which cause periodontal disease is, however, impossible.

Examples of a periodontal procedure are evident from U.S. Pat. Nos. 5,422,093; 5,234,940; 5,211,938 and 5,079,262. These involve the identification and subsequent treatment of malignant and nonmalignant tissue abnormalities using aminolevulinic acid. This is used in the form of an aqueous active substance solution. Excitation of cell fluorescence in the violet region (375 nm to 440 nm) leads to a red fluorescence being observed. An observation filter is used to filter out the diffusely reflected blue-violet excitation light, and the metabolically active tissue region is seen red against a background which appears slightly greenish (intrinsic fluorescence of the healthy tissue).

The rate constant with which metabolism takes place in the cells makes it necessary for the active substance to remain over a prolonged time (at least 15 minutes, typically 120 minutes) essentially unchanged in contact with the tissue.

SUMMARY OF THE INVENTION

The invention is therefore devoted to the problem of obtaining, in a simple manner at low cost and rapidly, information about the extent of a periodontitis, in particular also being able reliably to identify periodontitis in the initial stage.

To solve this problem, the invention indicates a material for differently modifying the optical properties of different cells (healthy tissue, diseased tissue, bacteria) which comprises firstly a substance which modifies the optical properties and secondly a basic material which is mechanically stable for a prolonged period under the conditions prevailing at the sites affected by periodontitis in a patient, and thus can release the modification substance over a prolonged period at the desired site. The proposed basic materials which are stable over a prolonged time under use conditions are viscous fluids, a gel, a two-dimensional or three-dimensional porous substrate or a material which hardens in situ (for example plastic film).

Materials which have different effects on different cells in a property typical of them are known in other medical sectors. Thus, for example, radioactive traces are used to identify cancer cells because they accumulate preferentially in the latter because of the greater metabolic turnover. Other modification substances are those which intervene directly in cell metabolism, stated more accurately in porphyrin biosynthesis. Administration of suitable modification substances, which are described in detail hereinafter, leads to intensification of the fluorescence spectrum of metabolically active cells. This makes it possible for these cells also to be determined quantitatively and in their spatial distribution, and the therapy can then be planned on the basis of this information.

It has now been realized that the technique developed in another medical sector for identifying diseased cells can also be employed in the periodontitis sector if the basic material used does not mix quickly with saliva and thus keeps the modification substance at the required site. Suitable for this purpose according to the invention are fluids having sufficient viscosity, gels, flat porous substrates such as wovens, nonwovens and the like or else three-dimensional porous substrates which are able to take up in their cavities particles of the modification substance or a concentrated solution thereof and thus release the modification substance distributed over a prolonged period. Another alternative consists of materials which harden in situ, such as film formers which bind or entrap the modification substance on the surface.

Advantageous further developments of the invention are indicated in dependent claims.

The further development of the invention ensures firstly that the basic material remains stable under the conditions acting on it at the site of use, and in addition does not change the surroundings to be investigated.

The further development of the invention permits easy application of the material but, nevertheless, ensures that the material is dimensionally stable to the required extent after application. The further development of the invention is also advantageous in relation to good dimensional stability of the material after application.

A material is particularly suitable for filling tooth pockets with negligible displacement of fluid from the tooth pockets. This makes it possible to diagnose the condition of a tooth pocket particularly well before the treatment.

The further development of the invention makes it possible to see at least through thin layers of the material, and for exciting light to be passed through the material.

Basic materials are suitable for in situ application of a material layer with particularly good dimensional stability.

On use of a material it is possible to use the time during which the material must remain at the site of use simultaneously for therapeutic purposes. Typical times between application of the material and the diagnosis of the cells modified by the material are about two hours. Thus a good therapeutic effect is also obtained in this waiting period.

The further development of the invention is advantageous in terms of good stability of the material in the oral environment, and such a material causes a negligible change in the initial condition of the cells or tissue regions to be investigated, also in terms of the pH.

Basic materials have been tested in the dental sector for a long time and are distinguished by excellent dimensional stability and good shape adaptation. Such a material serves well for investigations on tissue regions which are readily accessible.

The further developments of the invention permit diseased cells to be identified simply by eye or with use of a camera. It is possible in this way to establish easily with the eye or a camera the intensity of the disease and the spatial distribution of the diseased tissue regions. Such a direct optical image of the disease is particularly helpful for planning a therapy.

It is possible with a material easily to distinguish between cells which differ in metabolic activity but otherwise resemble one another greatly.

Influencing heme metabolism, is particularly informative and significant for a wide spectrum of different cells. The further development of the invention also has the advantage that such modification agents are available from the, other medical sectors (identification of cancerous tissues) mentioned at the outset. The corresponding substances can be synthesized at relatively reasonable cost.

The modification agent modifies the incorporation of iron into protoporphyrin, that is to say the last precursor of heme.

The invention specifies preferred concentrations of the modification substance which are advantageous in relation to pronounced modification on the one hand and not too great a change in the cell environment.

An apparatus facilitates the application of viscous or pasty material.

With an apparatus according to the invention it is possible with the application needle simultaneously to measure the depth of a tooth pocket and, when the depth of the tooth pocket is known, read off how far the needle has already been moved into the tooth pocket.

On use of an apparatus according to the invention the material is introduced into the tooth pocket gently so that the initial conditions are disturbed only slightly.

With an apparatus according to the invention it is possible to bring the material through the gingiva as far as tissue regions adjacent to the inner surface of the pocket.

The further development of the invention according to the invention is advantageous in relation to particularly delicate metering of material.

A diagnostic apparatus according to the invention makes it possible to inspect the cells which have been modified differently by the modification substance in a tooth pocket without the need to open the tooth pocket widely.

An apparatus according to the invention is able automatically to evaluate the proportions of healthy and diseased tissue and the intensity of bacterial invasion.

With an apparatus according to the invention the lateral dimension of the working head of the apparatus which can be introduced into the tooth pocket is particularly small. It can thus also be used for filming narrow periodontal pockets.

An apparatus according to the invention is able to measure simultaneously the root neck of a tooth and the inner surface of a periodontal pocket located next to the latter.

An apparatus according to the invention allows sequential surveying of individual strip regions of the tissue areas to be assessed and simultaneously ensures that the individual strip images can be automatically combined to give an overall two-dimensional image.

The achievement of the further development of the invention is to hold the photoconverters and the image converters at a distance from the lateral areas of a tooth pocket.

It is also known per se about the sector, mentioned at the outset, of the treatment of malignant and nonmalignant tissue abnormalities that the modification substances which are used therein and intervene in porphyrin metabolism bring about a photosensitization preferentially of the diseased cells. This photosensitization can be used to damage, by intensive beaming in of light of a suitable wavelength, these diseased cells so that they die. Such procedures are used in particular for the treatment of bladder carcinomas, brain tumors or carcinomas of the oral cavity.

The invention indicates an apparatus which utilizes for therapeutic purposes a photosensitization of diseased cells which has taken place in periodontal pockets.

On use of a flat light source for the therapy it is possible with an apparatus according to the invention to shield healthy tissue regions in the vicinity of a diseased tissue region from the therapeutic light and thus preclude damage to these regions.

The further development of the invention facilitates on the one hand the attachment of the mask parts and furthermore ensures that the mask parts also remain in the correct position during a prolonged treatment.

The choice of the wavelength of the therapeutic light according to the invention is advantageous in relation to maximally effective use thereof.

If it is wished to beam therapeutic light into a periodontal pocket through the open end of the latter, there is firstly the disadvantage that the periodontal pocket must be held open during the prolonged treatment, which causes pain, and secondly that the interior of the periodontal pocket is possibly not irradiated uniformly. The further development of the invention permits therapeutic light to be supplied two-dimensionally from the side through the gingiva. This eliminates the risk of shadows in the irradiation area.

With an apparatus according to the invention therapeutic light which is reflected from the tissue surface to be treated or from tissue located behind this is reflected a second time into the treatment zone. This results in a better yield of therapeutic light.

The achievement of the further development of the invention is that the therapeutic light reaches the site of administration with small scattering and refraction losses.

The further development of the invention is advantageous for larger irradiation areas because the therapeutic light is uniformly distributed.

The further development of the invention offers the advantage of a very high luminance for a short time but on average only slight thermal stress on the irradiated tissues.

The further development of the invention is advantageous in relation to protection of the applied modification material from interfering environmental effects.

An apparatus according to the invention can be used both as diagnostic apparatus and as therapeutic apparatus, it being necessary for changing over between these two modes of operation only to change the different filters placed in the light path between white light source and irradiation site.

The further development of the invention is advantageous in relation to effective feeding of light into a periodontal pocket. In this case it is unnecessary to open the periodontal pocket widely, and it is possible, by moving the light output element in a direction which is circular relative to the tooth axis (peripheral direction) also to carry out irradiations of different strengths according to a previously measured spatial distribution of the diseased cells, where appropriate at different sites of the root neck or the inner surface of the tooth pocket.

In this connection, the further development of the invention is advantageous when a larger irradiation area is desired with small dimensions of the light output element.

With the further development of the invention, refraction and scattering losses on inner boundary area which lie between the light output element and the area to be irradiated are kept small.

BRIEF DESCRIPTION OF THE DRAWINGS

The invention is explained in detail below on the basis of exemplary embodiments with reference to the drawing. In this.

DETAILED DESCRIPTION OF AN EMBODIMENT OF THE INVENTION

Figure 1:
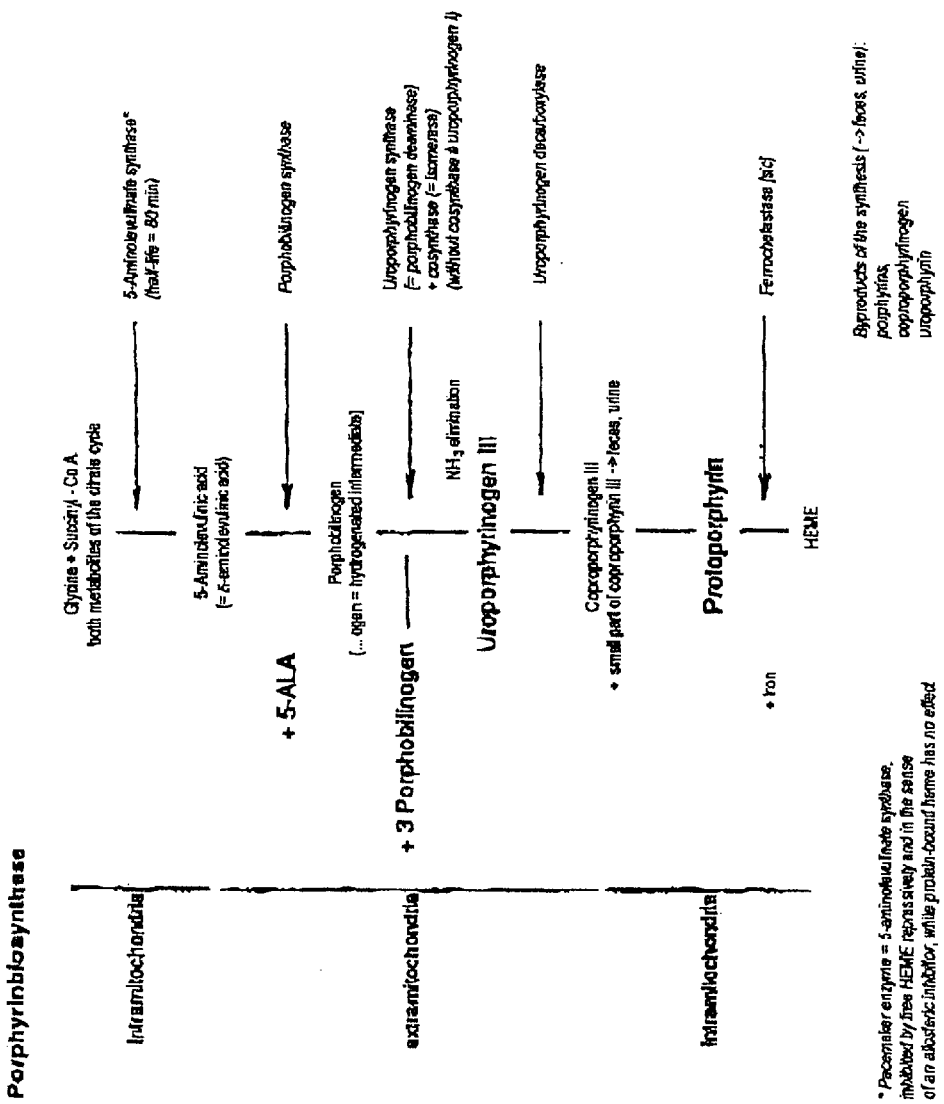
FIG. 1 shows a section of the heme circulation on the basis of which the photosensitization- of cells is illustrated.

FIG. 1 shows a section of porphyrin biosynthesis in a eukaryotic cell. The fluorescent substance which permits cells with enhanced metabolism (usually diseased cells) to be distinguished from normal cells is the protoporphyrin which is present before the last synthetic step. An increase in the amount of protoporphyrin present in a cell can be achieved firstly by increasing the concentration of the starting material of a precursor which increased protoporphyrin formation, or by reducing protoporphyrin breakdown by reducing the amount of iron available for the last synthetic step. Substances which act in the latter sense are referred to in the patent claims and hereinafter as modification substances.

In the part of the heme cycle which is evident from FIG. 1, the 5-aminolevulinate synthase involved in the first synthetic step depicted is a pacemaker enzyme. This means that this enzyme controls the overall rate of the subsequent part of the synthesis. For this reason, other reactants which take part only in earlier synthetic steps which are not depicted in FIG. 1 are ruled out as modification substances. On the other hand, suitable reactants are those which take part in that part of the synthetic chain which lies between 5-aminolevulinic acid and protoporphyrin (including these substances).

The individual synthetic steps are evident in detail from FIG. 1, as are the molecules involved in them. To this extent it is possible to dispense with a detailed description of FIG. 1. Reference should also be made to the effect that 5-aminolevulinate synthase is inhibited in its effect by free heme repressively and by allosteric inhibition (that is to say twice). Protein-bound heme has, by contrast, no such inhibitory function. The heme cycle is automatically controlled in this way. The pacemaker function of 5-aminolevulinate synthase is evident from the comparatively short half-life of only 80 minutes.

The modification substance currently preferred is synthetic 5-aminolevulinic acid hydrochloride which is obtainable commercially without difficulty (Merck, Art. No. 124802-0500; L 326102).

It is clear from the above descriptions that the waiting time between application of the material containing the modification substance, which is about 2 hours in the case of aminolevulinic acid, until diagnosis can take place can be shortened by using more advanced metabolic intermediates of the synthesis, for example porphobilinogen, uroporphyrinogen III or coporphyrinogen III. Also very suitable is uroporphyrinogen I or its metabolic precursors, which leads to more pronounced photosensitization and is therefore particularly suitable also for therapeutic purposes.

Other modification substances which can be used are agonists and/or antagonists of the metabolic enzymes. For example, a cosynthase inhibitor with simultaneous administration of the starting substances, for example of aminolevulinic acid, promotes the formation of the metabolite uroporphyrinogen I with subsequent modified metabolic parts. This results in improved photosensitization of the regions which show increased deposition of these metabolic products.

Substances influencing the breakdown of protoporhyrin [sic] which should be mentioned are ferrochelastase [sic] antagonists or iron complexing agents such as deferoxamine. These increase the amount of protoporphyrin appearing in the fluorescence on defined addition of the other metabolic products (where appropriate also in addition to an increased protoporhyrin [sic] formation due to other substances).

After the details of the modification substances which can be used have been set forth above, the basic material is explained in detail below.

The basic material has the task of keeping the modification substance in the vicinity of the tissue region to be treated or of the cells to be modified. For this reason, the basic material should according to the invention have dimensional stability. This does not mean dimensional stability in the sense of solid bodies or bodies fabricated from elastomeric material, but means a dimensional stability better than that of low-viscosity fluids such as water, alcohol etc. In this sense, dimensionally stable materials are also oil-like substances or gels.

In this connection, hydrophilic basic materials have the advantage that they combine well with the neck of the tooth or the inside of the pocket, whereas hydrophobic materials are kept floating in the pocket fluid or, if they are oil-like materials, may displace the sulcus fluid if this is desired in order to diagnose only the bacteria adhering to the neck of the tooth and the inside of the gingiva.

A first group of suitable basic material are substrates having cavities. The modification substance itself or a solution of the modification substance in a polar or nonpolar solvent can be taken up in the cavities thereof, the viscosity of any solutions used being chosen according to the structure of the cavities of the substrate and according to the chemical nature of the substrate material in relation to the desired length of the modification substance delivery time.

Examples of three-dimensional open-pore substrates are, for example, substrates which are formed by arrangements of small tubes, structured foams, sintered materials (also of organic materials such as PTFE) etc.

Examples of two-dimensional open-pore substrates are wovens, knits, nonwovens, scrimns.

The modification substance, if it is present in solution, is incorporated into these open-pore substrates by capillary action and/or the action of pressure. If the modification substance is in solid form (for example powder), it can be combined with the open-pore substrate by mechanical working (for example rolling in mechanically, in which case the particle solution and modification substance interlock mechanically with the substrate. Modification substance in powder form can also be compressed or combined using a binder with basic material in powder form.

A second group of substrates have a closed surface. Examples are plastic sheets, for example polyethylene sheets. Other examples of two-dimensional substrates are membrane-like structures.

With them it is possible to combine of the particles of the modification substance with the substrate using adhesives which are at least temporarily stable under the use conditions, or else briefly heat a substrate which can be softened and is fabricated, for example, from thermoplastic material, so that it enters a tacky state, and blow the material of the modification substance which is in powder form onto the tacky surface. It is possible analogously with other plastic materials to bring the surface of the substrate into a tacky state by partial chemical dissolution, and then likewise to pass powder as modification substance onto the surface.

Another group of basic materials are water-soluble gels. The modification substance can be incorporated even in high concentration into the latter.

It is important that such gels is [sic] not dissolved too quickly before delivery of the modification substance and before the necessary metabolic action time has elapsed, and is washed out of a periodontal pocket. The gel (all its ingredients apart from the modification substance) should have no adverse effect on the metabolic activity or vitality of bacteria or defense cells.

It is possible to use inorganic gels (gelation through addition off thixotropic fillers such as pyrogenic silicon dioxide or aluminum dioxide [sic]) and/or organic gels (for example hydroxyethylcellulose gel etc.). Substances like modified waterglass can also be used. (Inorganic) glycerol-based thixotropic gels are preferred.

Other basic materials are materials which harden in situ, in particular coating or film-forming substances which contain the modification substance and are applied in situ, where they form a film resistant to the surrounding medium.

Another alternative consists in putting modification substance in powder form or a modification substance solution into a microbag with permeable walls.

The modification material consisting of basic material and modification substance contains the modification substance in a proportion of about 0.5 percent by weight up to about 50 percent by weight. Preferred concentrations are between 5 percent by weight and 40 percent by weight, further preferably between 10 and 20 percent by weight.

It is common to the modification materials described above that they can be applied at the site of use without additional introduction of considerable amounts of fluid, so that they do not wash out motile bacteria found in the periodontal pockets, and it is thus possible to measure unfalsified starting conditions. The modification substance becomes distributed by diffusion uniformly in the periodontal pockets as far as the base of the pocket and into the interradicular regions. With the modification material composition mentioned above there is little or no adverse effect on the medium present in the periodontal pocket either.

The process for a diagnosis using a modification material of the gel type is now described in detail below.

In the initial diagnosis of a patient for periodontal disease or in a check of findings in the sense of monitoring, firstly the depths of the pockets surrounding the individual teeth are measured, usually each at different sites and also in the region of any tooth furcations. This is done using a periodontal probe which is introduced into the pocket with a defined pressure as far as the fundus of the pocket. Immediately after removal of the probe, the findings "bleeding on probing" and "pus emergence" are recorded and correlated with the degree of inflammation. In this classical procedure, the contents of the tooth pocket are slightly changed by the probing. The way to avoid this is described in detail below.

In order to avoid inactivation due to light exposure or interactions with the hydrolytic gel, the gel is mixed and combined with the modification substance only shortly before use. The gel is adjusted to a pH in the slightly acidic to neutral range, for example in the range between pH 4.5 and pH 7.5. Adjusting the pH to about 5 has proved particularly advantageous.

To avoid inactivations during the storage time and with a view to extending the storage time, the modification substance is stored separately from the basic material and, where appropriate, in a buffer solution (for example citrate buffer). One advantageous possibility for storage is that in a two-chamber cartridge which is activated immediately before use by perforating the partition between the two chambers. The two components are then mixed together, for example in a mechanical shaking mixer as is available in dental practices. Alternatively, modification substance in powder form can also be mixed on a sterile plate with the basic material and then introduced, for example with a sterile spatula, into an applicator or dispenser. The latter type of procedure makes it possible for the user to choose the amount of modification substance incorporated into a modification material differently according to his particular requirements.

The modification material produced in this way can then be introduced with a rod-like tool into the pocket and distributed there, and application preferably takes place with a needle.

The modification material is then left to act for about two hours on the cells to be investigated. Metabolism takes place there, in particular, as explained above, more strongly in metabolically active cells.

After this action time, the investigation region is irradiated with an exciting light (violet exciting light in the case of 5-aminolevulinic acid) which is produced, for example, by filtering out the appropriate wave region from the light of a white light source (for example halogen lamp, xenon lamp). The fluorescence generated by the exciting light is observed using a filter located [lacuna] for the measurement light, either directly or using a television camera. Information about the amount and distribution of diseased cells in the tooth pocket, and thus about the extent of periodontitis, is obtained in this way. It is thus learnt where particularly affected tissue regions are located, and it is possible to take these into account in a particular manner in the subsequent therapy.

Residues of the gel which are still present, and modification substances released by the latter, are then washed out of the pocket.

Another exemplary embodiment may consist of, for example, impregnating paper with a solution of the modification substance and cautiously pushing the impregnated paper into the tooth pocket. The modification substance is then released there and metabolized. After a sufficient action time, the paper is removed and the fluorescence from the pocket is analyzed.

In a further modification it is also possible to place modification material directly in the immediate vicinity of the pocket inlet. In this case, owing to the concentration gradient of the modification substance the latter migrates into the pocket.

As explained above, determination of the depth of the pocket is always the first finding to be recorded. This determination inevitably leads to a slight change in the contents of the pocket. If it is wished to avoid such a change, it is possible on the one hand to provide the determination of the depth of the pocket as last step in recording the findings, but it is then necessary in some circumstances to dispense with recording of the findings "bleeding on probing" and "pus emergence".

For this reason, it is proposed to combine the measurement of the depth of the pocket and the application of the modification material in one step. This is done by providing an application needle also with a gradation which allows the depth of the pocket to be measured. This is described in more detail below.

The equipment aspect of the invention is now explained in detail below, referring to FIGS. 2 to 9.

Figure 2:
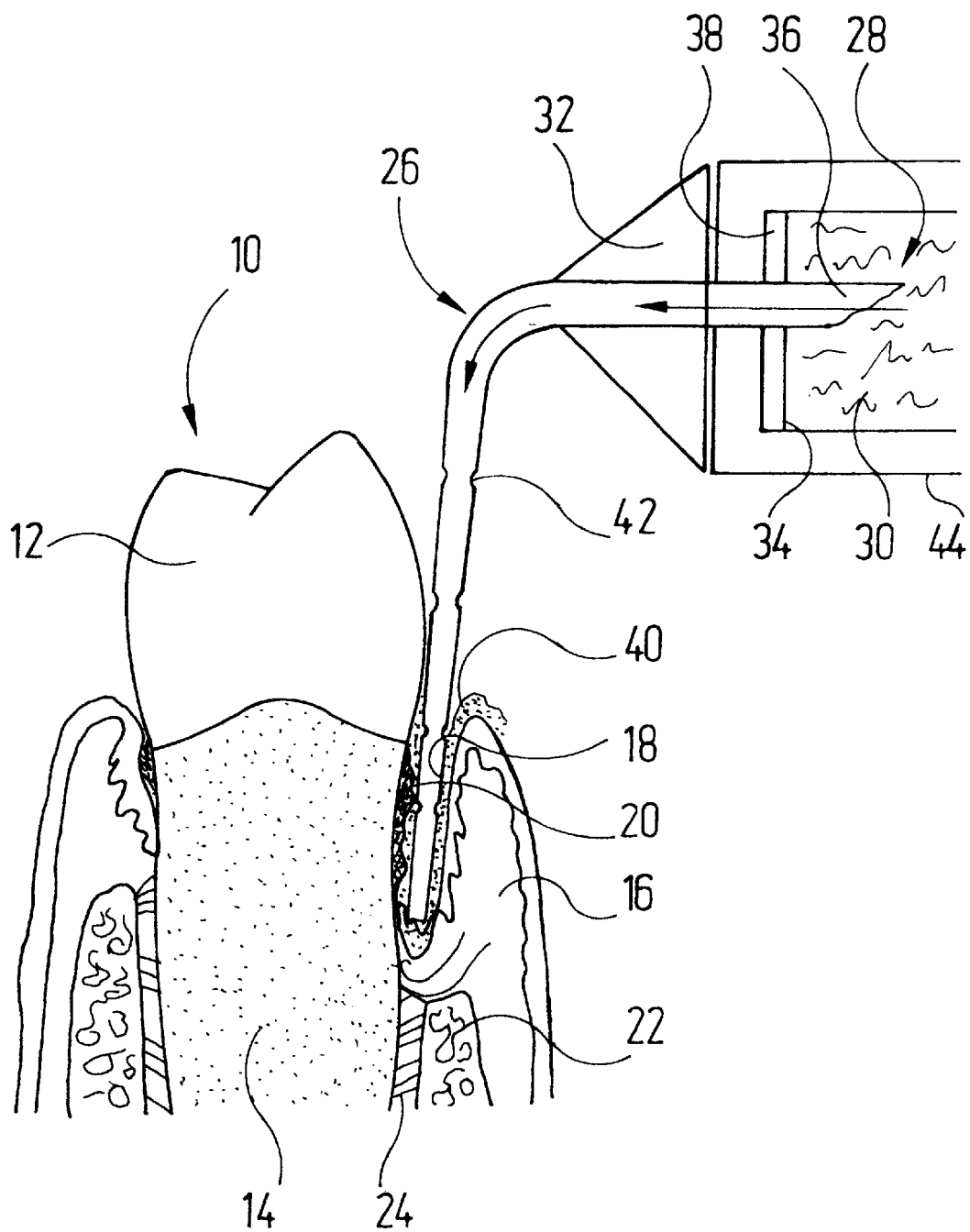
FIG. 2 shows an axial section through a tooth and adjacent soft tissue, and a lateral view of an applicator for material bringing about photosensitization of diseased cells or of bacteria.

Reference numeral 10 in FIG. 2 designates a tooth which has a crown 12 and a root 14. Reference numeral 16 designates the gum (gingiva) surrounding the tooth. A periodontal pocket 18 has formed at the upper end of the root 14 between the root and the gum 16. A calculus layer 20 has formed on the neck of the tooth.

Between a section 22 of the jawbone and the root there is a layer 24 of periodontal fibers.

A needle which is designated overall by reference numeral 26 is introduced into the periodontal pocket 18 and is connected to a cartridge 28 which contains a modification material 30. For connection to the cartridge 28, the needle 26 has a fastening part 32 which is connected to the cartridge housing which is designated by 34. A pointed end section 36 of the needle 26 is introduced through a sealing wall 38 of the cartridge housing 34 into the modification material 30.

The modification material 30 can be forced through the needle 26 into the periodontal pocket 18 by manually moving a displacement piston which is not depicted in the drawing. An applied amount of modification material 30 which is present in the periodontal pocket 18 is designated by 40 in the drawing.

If the needle 26 is positioned so that its lower end is adjacent to the base of the pocket it is also possible to measure the depth of the periodontal pocket on marks 42 attached to the outside of the needle at the same time as introducing the modification material into the periodontal pocket.

For uniform filling of the entire periodontal pocket 18, the needle is moved in the periodontal pocket 18 in the peripheral direction relative to the axis of the tooth 10 and while maintaining the alignment of the needle parallel to the axis, so that the pocket is uniformly filled with modification material and, at the same time, surveyed for its depth.

If required, an X-ray contrast agent can also be added to the modification material at the same time and, after the introduction of the modification material, the contour of the periodontal pocket 18 can be recorded by an X-ray film.

Figure 3:
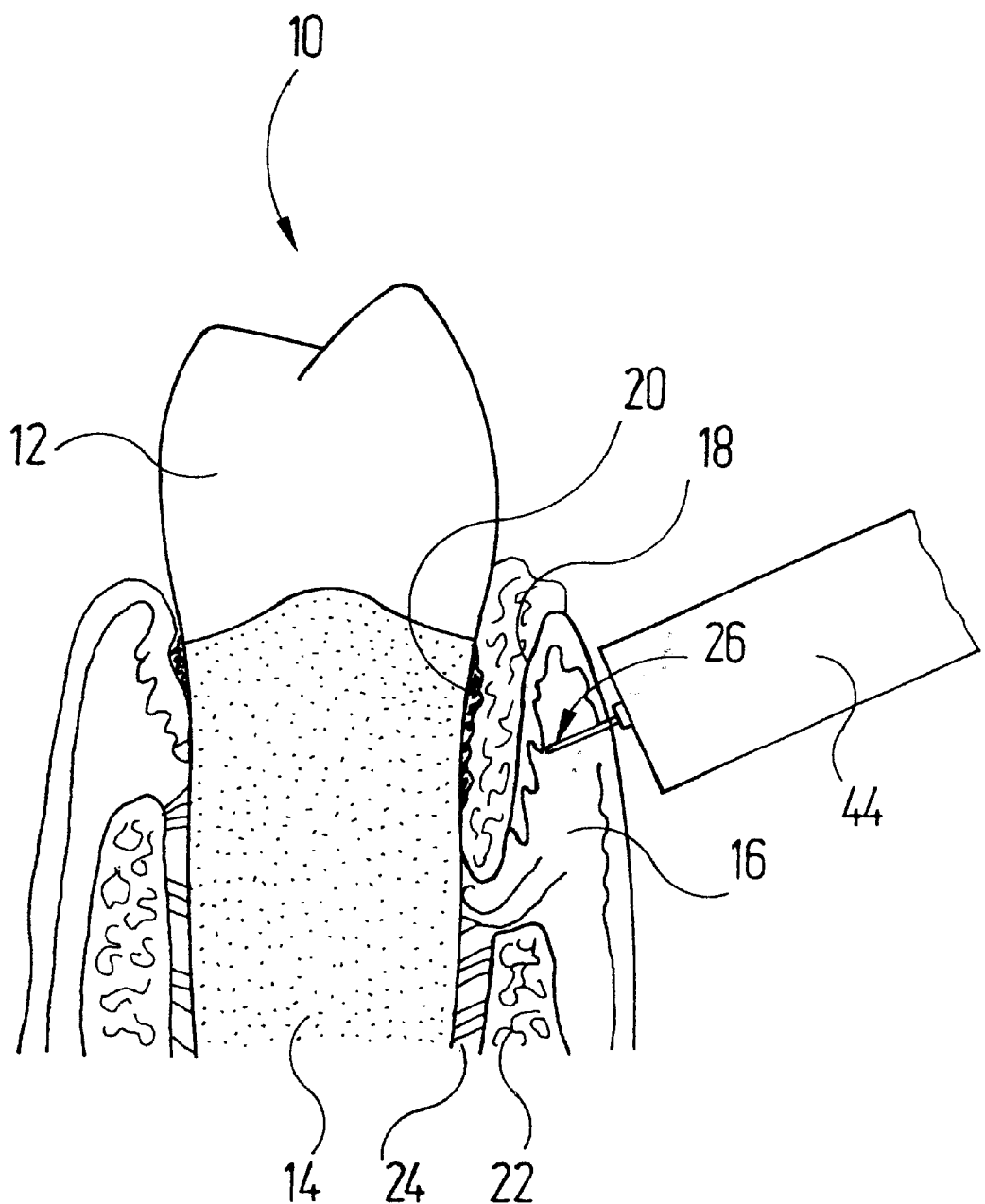
FIG. 3 shows a similar depiction as FIG. 2, but representing a modified applicator.

Alternatively, as shown in FIG. 3, a short thin and sharp needle 26 can be used in conjunction with a liquid modification material, and the modification material can be injected through the gum 16 into the periodontal pocket 16 [sic] or into the regions of the gum 16 adjoining the latter. With this type of procedure, the contents of the periodontal pocket 18 remain unchanged. The modification substance again reaches by diffusion the inner surface of the periodontal pocket and the contents of the pocket. The further procedure after the injection of the modification material is the same again as described above.

Figure 4:
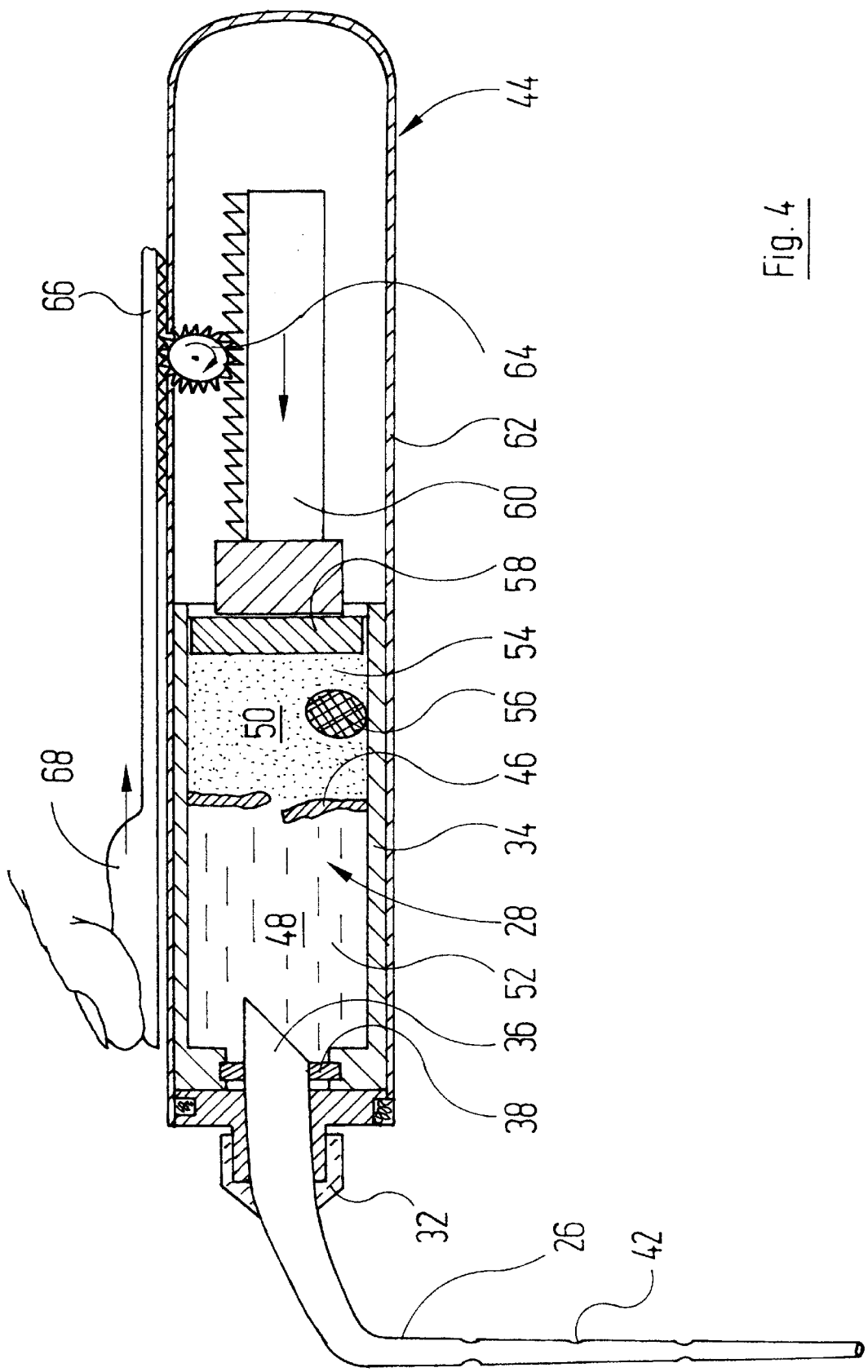
FIG. 4 shows an axial section through an applicator which has been modified again, similar to that of FIG. 2.

FIG. 4 shows a practical exemplary embodiment of an applicator 44 for modification material having high viscosity. Parts already mentioned with reference to FIG. 2 are provided with the same reference numbers again.

The cartridge 28 has in the middle a partition 46 which can be destroyed and which divides the interior of the cartridge into two chambers 48, 50, of which one (chamber 48) contains the basic material 52, and the other (chamber 50) contains the modification substance 54. One of the chambers (in this case chamber 50) contains a bead 56 which serves to break open the partition 46 by hitting the cartridge against a hard surface and to mix the contents of the two chambers 48 and 50, as usual with two-chamber cartridges. Depicted at the rear end of the cartridge 28 is a displacement piston 58 which is connected to a rack 60. The latter is coupled via a pinion 64 which is mounted on a housing 62 of the applicator to another rack 66 which is mounted on the applicator housing 62 and can be moved in the longitudinal direction thereof. The rack 66 is connected to an actuation part 68.

Modification material [lacuna] discharged through the needle 26 by pushing the actuation part 68 in FIG. 4 to the right after breaking open the partition 46 and mixing the contents of the two chambers 48, 50.

In a modification of the exemplary embodiment described above, the actuation part 63 can also be connected directly to the displacement piston 58, which reverses the actuation direction of the applicator 44.

Observation of the fluorescence of the diseased cells or bacteria can in principle take place by lifting the periodontal pocket 18 up locally with a suitable instrument, illuminating the entire region of the periodontal pocket 18 with the exciting light of 375 nm to 440 nm, and viewing with the eye the red fluorescence directly with the eye [sic] through an observation filter which is transparent in the region of the red emission spectrum of the fluorescent protoporphyrin The implement used to abduct the gum is then moved in a circular direction in order to inspect the various sections of the periodontal pocket successively. In this way, a picture of the extent of the periodontitis and of the spatial distribution of the diseased areas is obtained. The background light which is seen as subdued green in this case permits spatial assignment of the fluorescent regions to the individual dentition situation.

If required, with this direct visual inspection of the fluorescence it is possible for an observation filter which is transparent in the red to be incorporated into spectacle frames worn by the clinician or to be designed as an attachment in front of spectacles. Alternatively, the observation filter can be attached to a different part, for example to the implement used for partial opening of the periodontal pocket, to any light guide used to supply the exciting light, or as elastic filter which adapts elastically to the surroundings with adaptation of a light guide and thus can be provided directly at the point of emergence of the fluorescent light. If a video camera is used for observation, the observation filter can be placed on its lens.

Figure 5:
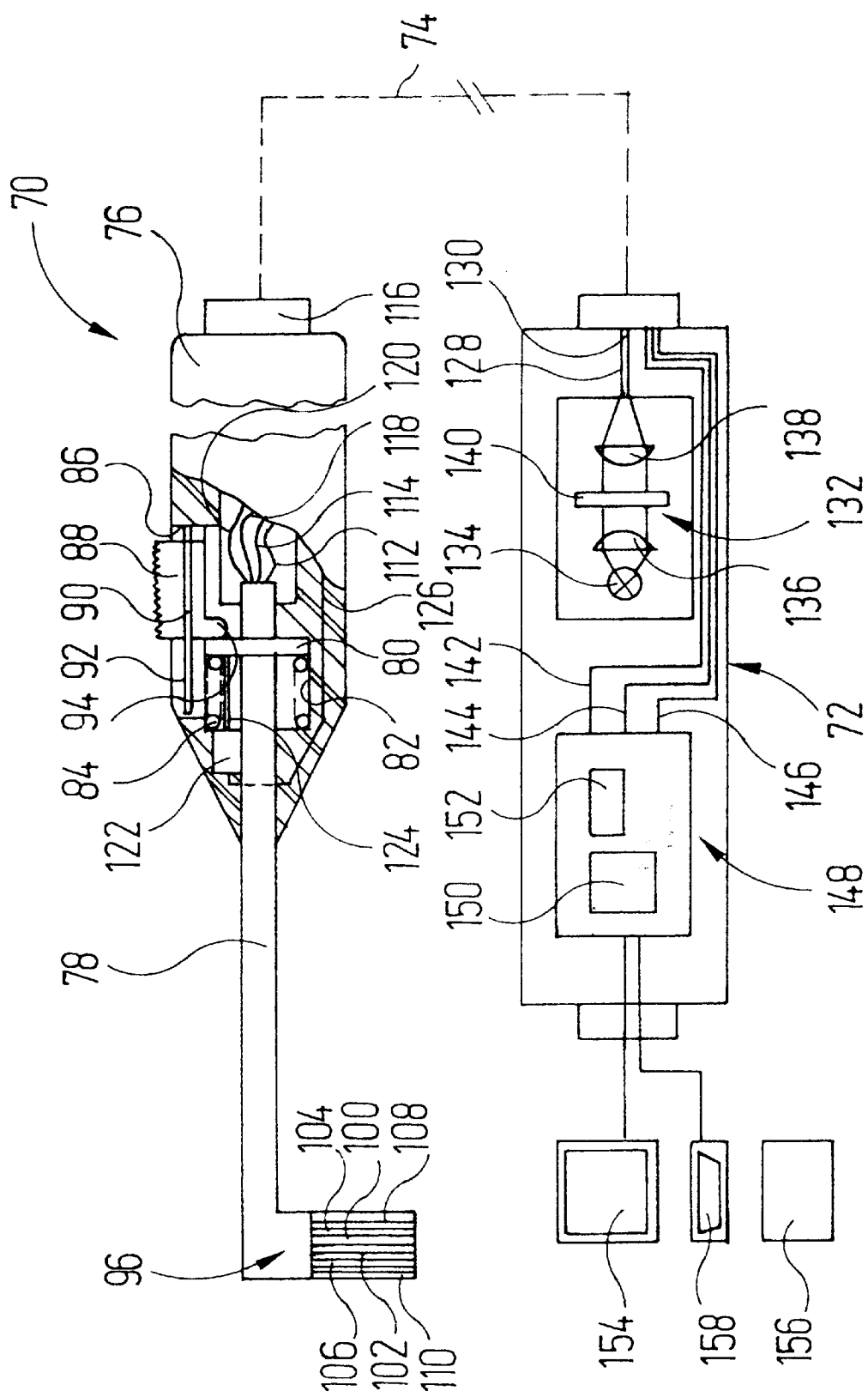
FIG. 5 shows an axial section through a diagnostic apparatus for measuring the spatial distribution of diseased cells in a tooth pocket, and the assigned evaluation electronics.
Figure 6:
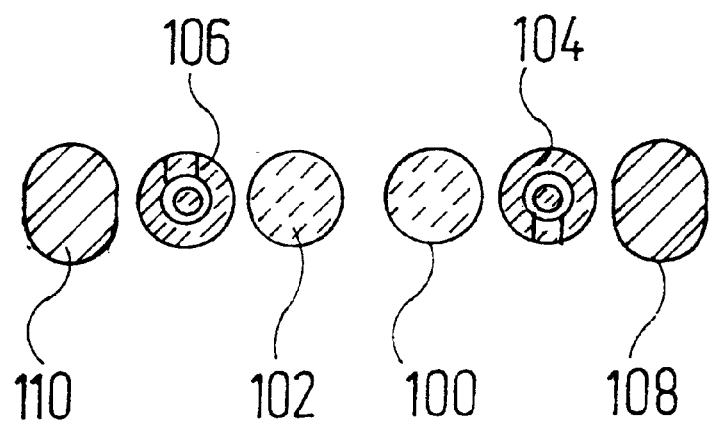
FIG. 6 shows a transverse horizontal section through the sensor head of the diagnostic apparatus shown in FIG. 5 on an enlarged scale.

For simple illumination and inspection of the interior of the periodontal pocket, it is also possible to use a diagnostic apparatus as depicted in FIGS. 5 and 6. This diagnostic apparatus consists of a handpiece which is designated overall by reference numeral 70 and of a supplier and evaluation unit 72 which is designated overall by reference numeral 72 and which is connected to the handpiece 70 by a cable 74.

The handpiece 70 has a grip part 76 in which a bar 78 having a rectangular cross section is displaceably mounted. The bar 78 has a flange 80 which is displaceable in a spring chamber 82 and is pretensioned by a helical pressure spring 84 in a retracted position to the right in the drawing.

A sliding part 88 can be displaced in a recess 86 in the grip bar 76 and has on its two lateral surfaces guide ribs 90 which cooperate with matching guide grooves 92 in the lateral surfaces of the recess 86. The sliding part 88 has a catch 94 which cooperates with the flange 80.

The front end, which is located on the left in FIG. 5, of the bar 78 has a working head 96 which has only small dimensions in the direction perpendicular to the plane of the drawing in FIG. 5, for example is 0.5 mm to 1 mm thick.

The working head 96 comprises rod-like elements which are located in the plane of the drawing in FIG. 5 and follow one another closely, every second of which is a light output element fabricated of a material which is transparent for the exciting light, two of which are show in the drawing at 100 and 102, and the others are line image converters, of which two are shown at 104 and 106. One of, these points its active side forwards and the other backwards.

In the depicted exemplary embodiment, the line image converters 104, 106 are located on both sides of the light output elements 100, 102. In a modification, it is also possible to provide only one single light output element, which is then arranged between the two line image converters. Rod-like spreading elements 108, 110 are located on both sides of the arrangement formed by the light output elements 100, 102 and the line image converters 104, 106 and have somewhat larger dimensions in the direction perpendicular to the plane of the drawing in FIG. 5 than do the light output elements and line image converters, for example are 0.2 mm larger than the latter. In this way, the forces acting on the light output elements [lacuna] line image converters on displacement of the working head 96 into a tooth pocket are kept small.

The light output elements 100, 102 are connected to light guides 112, 114 which are embedded in the bar 78 and are connected via flexible light guide sections, which have slack, to connections of a plug connector part 116.

The line image converters 104, 106 are connected to cables 118, 120 which likewise extend through the bar 78 and are connected via cable sections, forming slack, to assigned connections of the plug connector part 116.

A position indicator 122 is provided to determine the instantaneous position of the bar 78, and its rod-like input past 114 cooperates with the rear side of the flange 80. The output signal from the position indicator 122 is passed via another line of the cable 74 to another connection of the plug connector part 116.

The various connections of the plug connector part 116 are connected via the cable 74 to the supply and evaluation unit 72. The cable 74 contains two light guides 128, 130, whose ends are joined at a point, for supplying light to the light output elements 100, 102. This point is connected to the output of an exciting light source which is designated overall by reference numeral 132. The latter comprises a white light source 134 which can be formed, for example, by a xenon short-arc lamp, a double collimator 136, 138 and a color filter 140 which can be placed in the latter and which is transparent in the violet.

The cable 74 additionally contains three lines 142, 144, 146, which pass the output signals of the two line sensors 104, 106 and the output signal of the position indicator 122 to assigned inputs of a computer 148. The latter comprises inter alia a CPU 150 and an image store 152.

Roughly speaking, the computer operates in such a way that it files the [lacuna] from the line sensors 104, 106, addressing a signal derived from the output signal of the position indicator 122, in the image store 152 so that a two-dimensional image of the outside of the neck of the tooth or the inside of the periodontal pocket is obtained in the image store 152 by moving the working head 96 on the sliding part 88 while holding the grip part 76 unchanged, for example supported on adjacent teeth.

The computer 148 is also able to determine, taking account of the number and intensity of pixels whose color corresponds to the fluorescent light, what proportion of the surveyed surfaces is diseased or affected.

The computer 148 is also able to carry out conventional image processing in order to sharpen the contrast, alter the scale of the image etc.

The computer 148 is able to output the images, which have been reworked where appropriate, on a screen 154 or a color printer 156. A keyboard 158 serves for adjustment of the image analysis required in each case.

It is evident that the diagnostic apparatus shown in FIGS. 5 and 6 is able to give an image of the region of the neck of the, tooth which predetermines the one side of the tooth pocket, and of the part of the gum adjoining the other side of the pocket, under the restricted conditions in a tooth pocket with negligible deformation of the tissue adjoining the tooth pocket.

With the exemplary embodiments described above, the modification material was used to mark diseased regions via their optical properties and thus make a visual check thereof possible. The modification material can, however, also be used for therapeutic purposes. The modification material is again placed, in any one of its embodiments described above, on the diseased sites. After an action time of at least 60 to 80 minutes, preferably about 120 min, the diseased cells are photosensitized as has been described above. These photosensitized cells can now be damaged by intense irradiation with light to such an extent that they die. For this purpose it is possible to allow, for example, white light to act with an illumination of 0.3 W/cm$^2$ for a period of 1 min, which results in a significant reduction in vital bacteria in the periodontal pocket, which persists for periods of several weeks.

Such an intense irradiation with white light also adversely affects healthy tissue regions, although they are not damaged so much that they die. In order to avoid or minimize such temporary tissue damage it is possible to use mask parts which cover the adjacent healthy tissue regions during the irradiation.

Figure 7:
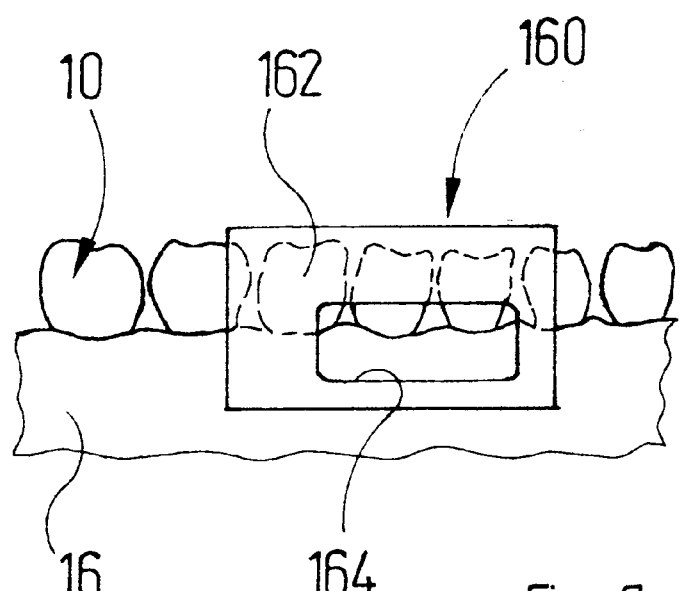
FIG. 7 shows a mask part as used for pergingival irradiation of a periodontal pocket.

FIG. 7 shows such a mask part 160, which is designed like a guard so that it covers a plurality of adjacent teeth. The channel is preferably resilient so that the mask part 160 can be locked on the group of teeth with a side 162 of the channel located in front of the group of teeth and with a corresponding side located behind the group of teeth. A recess 164 defining the irradiation site is provided in the front side 162.

The mask part is preferably a disposable part thermoformed from plastic sheet, with black pigments being incorporated into the plastic material in sufficient concentration for the material to absorb white light well.

Figure 8:
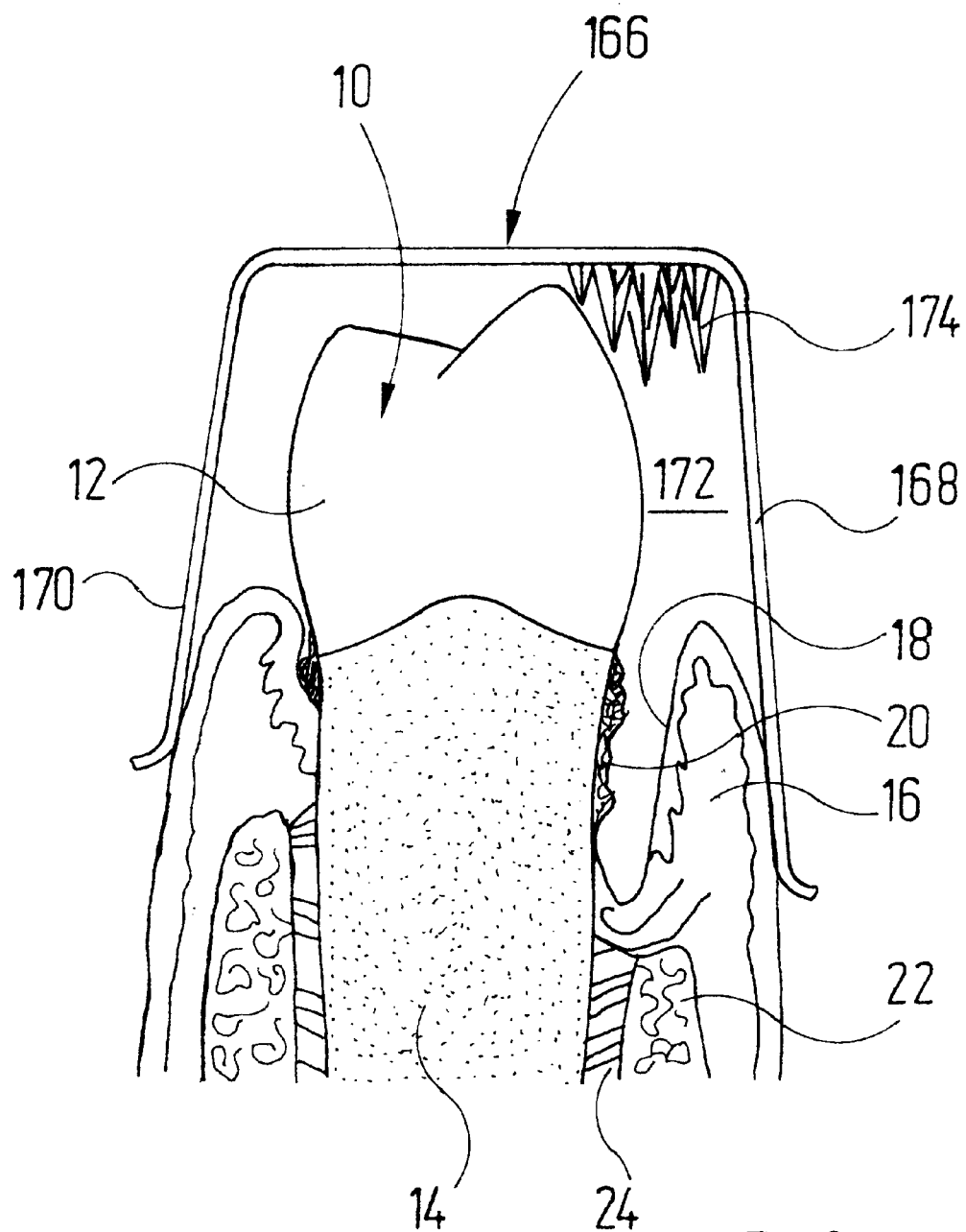
FIG. 8 shows a transverse section through a light distributor guard as used for therapeutic purposes.

In cases where a group of teeth are to be treated in the same way, it is possible as shown in FIG. 8 to provide a distributor guard 166 which is likewise placed on a group of teeth and has on the inner surface a highly reflecting layer. The distributor guard 166 has a side 168 located in front of the group of teeth and a side 169 located behind the group of teeth and is again elastically deformable and can thus be clipped onto the group of teeth. In this case, the sides are now however, each bent inwards, as indicated at 170, so that a light distribution channel 172 remains over the teeth. The therapeutic light is fed into the latter from one or both of the front sides. The side-connecting section 174 at the top of the distributor guard 166 has a plurality of, for example, pyramidal elevations 174 which project into the inside of the light distribution channel 172 and whose height increases from the end of the distribution guard to its middle (on irradiation from both sides) or from one end to the other end (beaming in light from one side). In this way, the consecutive tooth pockets are irradiated in the same way by a single irradiation procedure.

If longer-term irradiation is necessary, the tissue regions adjacent to the irradiation site which are to be protected can additionally be cooled by a fine water spray or by cooling air in order to preclude the pain which is occasionally experienced by the patient during photodynamic therapy.

The use of visible light requires free access to the area to be irradiated. This must often be created by lifting the gum away from the neck of the tooth, which is unpleasant for the patient. Where such an opening of the tooth pockets is unwanted, the photodynamic therapy can also be carried out from the side through the gingiva. This is done by using light which is only slightly absorbed or not absorbed by the water-containing gingiva. Infrared light or longer-wavelength electromagnetic radiation such as microwaves comply with this requirement.

In terms of the equipment setup necessary overall for diagnosis and photodynamic therapy, it is advantageous if the same apparatus can be used with small modifications on the one hand for diagnosis and on the other hand for therapy. This is possible with the apparatus shown in FIG. 5, by replacing the color filter 140 by another color filter which is transparent in a wavelength range favorable for the therapy. In this case, the therapeutic light is also supplied directly to the treatment site via the light output elements 100, 102. If it is wished to protect the line sensors 104, 106 from severe radiation exposure as is occasionally desirable in photodynamic therapy, it is possible to use for the therapy a modified handpiece which has only light output elements 100, 102, which are then provided in larger numbers.

In a further modification of the last-mentioned exemplary embodiment, the large number of rod-like light output elements 100, 102 etc. which are located side by side can be replaced by a single light output element in plate form. This can then be provided with scaly surface asperities or be provided in the volume with scattering centers such as metal particles, bubbles or the like (this measure can also be provided for the light output elements of the diagnostic working head 96), in order to ensure omnidirectional output of therapeutic light. The light output elements can also consist of an elastic material which is transparent for the therapeutic light, so that the light output elements can be adapted to the shape of the neck of the tooth or of the periodontal pocket.

It is possible analogously, in a modification of the exemplary embodiment shown in FIG. 5, also to use for a diagnostic handpiece flexible light output elements 100, 102 and flexible line sensors 104, 106, which adapt to the shape of the periodontal pocket.

If the dimensions of the working head 96 of a therapeutic handpiece as has been described above are small in the longitudinal direction of the bar 78, the various regions of the periodontal pocket are irradiated successively by displacing the working head. The irradiation time can then be used to take account of the particular diseased state of the periodontal pocket region which has just been treated. If working heads of greater length are chosen, it is possible to irradiate one periodontal pocket in one procedure, but specific account cannot be taken of regions diseased to different extents.

It is true both of diagnostic handpieces and of therapeutic handpieces when reflection and scattering losses on internal interfaces of the light path between light source and region to be illuminated or irradiated of the periodontal pocket or of the neck of the tooth are minimized. This can be done by providing coupling media with suitable refractive index between the light output elements and the regions to be illuminated or irradiated. Examples of such coupling media are transparent gels such as glycerol gel. If the periodontal pocket is sealed to the outside, it is also possible to use fluids such as water. The function of a coupling medium can also be fulfilled by hardening "gels" or plastics such as transparently polysiloxanes.

In a further modification of the exemplary embodiments described above, the modification material and/or the coupling medium may be mixed with other substances which either favor the subsequent course of the investigation (for example agents which stop bleeding) or are advantageous in terms of prophylaxis and/or medical therapy. Mention should be made here of fluorides, disinfectants such as chlorhexidine, desensitizing substances such as strontrium [sic] or potassium containing compounds, antiadhesives such as delmopinol or triclosan etc. It is possible in this way to use the time required for the photosensitization also for therapeutic or prophylactic measures.

Continuously operating light sources were used in the exemplary embodiments described above. It is self-evident that flashing light sources such as strobe lights can also be used in particular for photodynamic therapy. It is moreover possible in photodynamic therapy to reduce any pain reaction, and minimize the risk of thermal damage to surrounding healthy soft and/or hard tissues, by adjusting the ratio between the flash duration and the time between flashes. Such flashing light sources can be used both for direct illumination or irradiation or else for illumination or irradiation via light output elements introduced into the pocket or for illumination or irradiation of a multiplicity of tooth pockets through a reflecting distributor guard, as described above.

Figure 9:
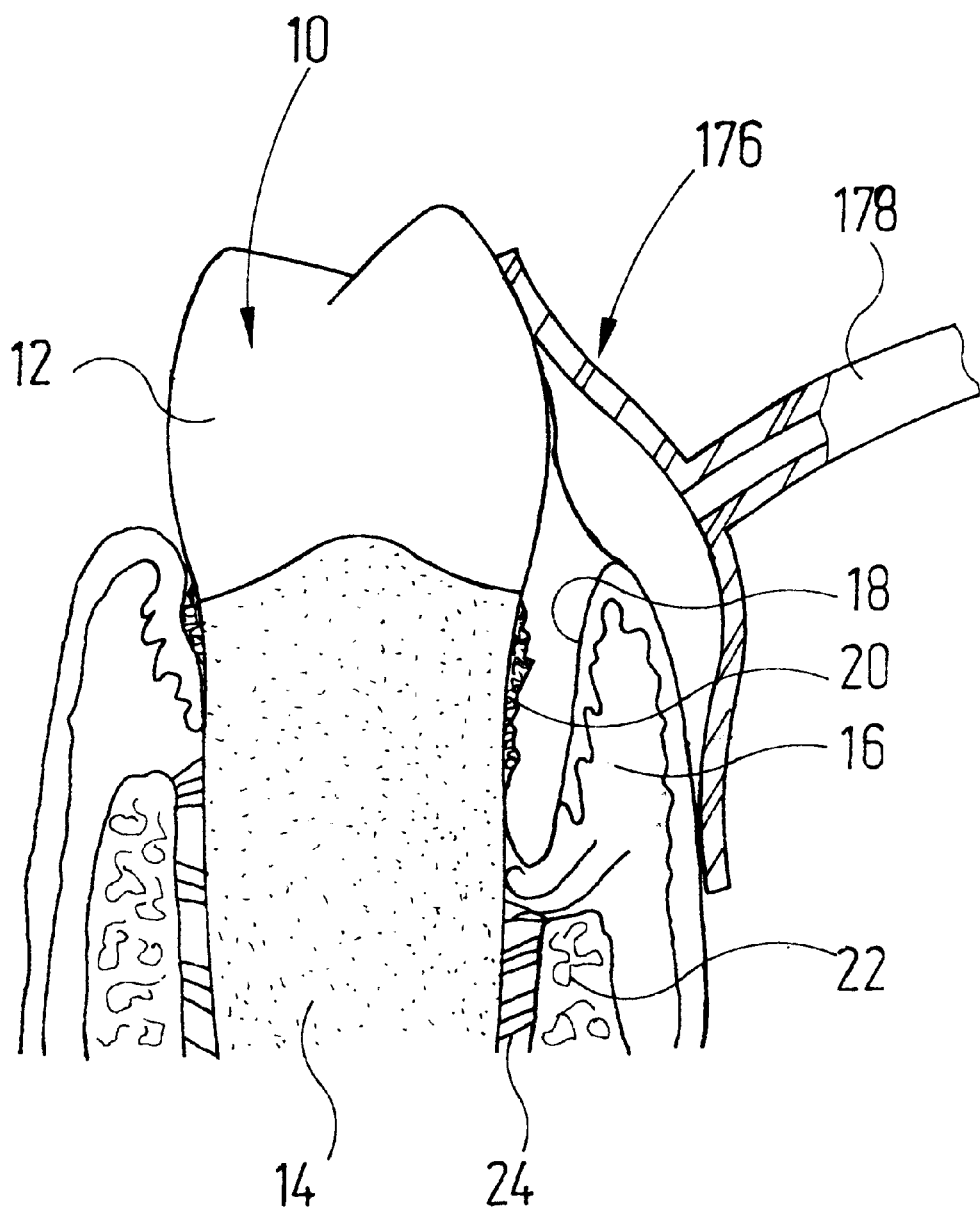
FIG. 9 shows a sealing cap by means of which material, which has been introduced into a gingival [lacuna] for modifying the optical properties of diseased cell, is sealed off from the oral environment during the exposure time.

As shown in FIG. 9, modifying material 40 introduced into a periodontal pocket 18 can be protected against fluid in the mouth and against release of modification substance into the oral cavity by sealing the upper open end of the periodontal pocket off from the oral cavity with an elastic protective cap 176. The latter can be attached mechanically, for example by a wire clip, to the tooth 10 or teeth adjacent thereto, or be held in place by reduced pressure, for which purpose it has a tube 180 which can be connected to a source of reduced pressure.

The invention has been described above with reference to photodynamic diagnosis and with reference to photodynamic therapy. In practice, these possible uses of the invention will be combined with other periodontal therapeutic methods, in particular with ultrasound therapy.

The photodynamic diagnosis according to the invention is advisable in parallel with any conventional periodontal diagnosis, in particular when there are findings leading to suspicion of established marginal periodontitis. After active lesions have been marked in fluorescence contrast as described above, subsequent photodynamic therapy is advisable in order to reach the inflammatory correlates and causative bacteria even in sections of the periodontal pockets which are not accessible to conventional mechanical methods or to an ultrasonic therapeutic method. It is thus possible by use of the invention for the first time to control effectively bacteria which have also infiltrated into the pocket epithelium and into adjacent connective tissues dispensing completely with antibiotics and substantially avoiding systemic side effects.

After completion of the photodynamic therapy (and, where appropriate, after renewed diagnosis), subsequently a conventional mechanical cleaning or rinsing of the affected periodontia is carried out, preferably an ultrasonic therapy is carried out. The latter has the great advantage that any residues of gel and photodynamically inactivated bacteria are removed particularly effectively from the pocket thereby. Any bacteria which have not been photodynamically inactivated are also effectively removed by the ultrasound-induced liquid shear movements, by gravitation, by evolution of heat or (in the case of bacteria adhesively bound to tooth or other tissue surfaces) by mechanical abrasion.

During the re-evaluation of the findings which is necessary with periodontal treatments, the diagnosis according to the invention is used again, by which means it is possible to assess the effects of therapy more differentially and with finer resolution than with previous diagnostic methods. This is a precondition for individual planning of the maintenance therapy in the sense of (re)infection control and periodontal prophylaxis.

The invention can also be made use of in the area of the diagnosis of caries lesion, especially at concealed sites in the region of fissure caries and approximal caries.

The diagnosis is performed in analogy to the above description of periodontal diagnosis. This is because the caries-causing bacteria (streptococci) are likewise metabolically active. Their acid production is the cause of the caries. The affected hard substance surfaces by contrast display no metabolism (in the sense relevant here), which is why good contrasts are produced between bacterial layers and the tooth surface. Although intrinsic fluorescence effects of the hard substance of the tooth are superimposed here in some cases, they are of only minor importance.

Application of the modification material must again take place in such a way that the modification substance is kept on the areas in question of the surfaces of the hard substance of the teeth for a time sufficiently long for metabolism under the surrounding conditions. Solvent-containing surface coatings, for example based on resins or wax, for example collophony, shellac etc., are therefore particularly suitable as basic material. Hydrophilic substrates which adhere well to the surfaces of the teeth for the time necessary for metabolism, even with access of saliva, are preferred.

It is also possible initially to apply modification materials which comprise hydrophilic gels as basic material, as described above in connection with periodontal diagnosis, for example glycerol gel. These materials can then be coated with another material, preferably a surface coating of the type mentioned above, for long-term stabilization at the site under consideration.

Basic materials alternatively suitable for the modification substances to be metabolized by the bacteria or for coating initially applied modification materials are also plastics, for example siloxanes, polyethers, or else materials based on agar. Also suitable is protection of the applied modification material by applying an overimpression or by putting on an isolating guard which separates the model material from the interior of the oral cavity.

The use described above of the diagnosis according to the invention for identifying caries permits in critical cases the identification of an initial caries lesion, in particular after previous surface cleaning of adsorbed plaque from the affected surfaces of the teeth. This is attributable to the fact that the modification substance and the metabolic products diffuse into the surface edge zones or defects below the surface of the hard substance of the teeth, which makes quantifiable diagnosis of structural intrusions possible. Valuable information is thus obtained as a secure basis for a therapeutic decision. Quantitative evaluation of the fluorescence diagnosis makes it possible, in particular with interfaces of invasive diagnosis, to monitor the course in the sense of caries caries monitoring and, where appropriate, also to monitor therapeutically induced stagnation or remineralization. The use of video technology with suitable filters and subsequent image analysis is also advantageous in this application.

Unlike the periodontal application, in which floating plaque is present, which is easy to wash out of the periodontal pocket, cariogenic plaque firmly adheres to the surface of the tooth. For better infiltration of the modification substance into surface defects, therefore, application using a closed suction cap or an impression tray placed over the area to be investigated in a fluid-tight manner has proved suitable, in which case the penetration of the modification material into the surface defects can be assisted by alternating pressure application to the interior of the suction cap or the impression tray. This results in a pumping effect which is brought about by positive and negative pressure peaks.

The caries diagnosis according to the invention is also used particularly advantageously in the edge region of dental restorations. If incipient caries is identified there, it is possible by diffusion, assisted where appropriate by alternating pressure application as described above, of an active substance into edge fissures, which are leaky and colonized by bacteria, of fitted dental restorations to control effectively the caries in the initial stage and avoid remaking of the dental restoration. Leakage phenomena which make remaking of the dental restoration necessary in the long term can, in particular, be reliably identified by the fluorescent caries diagnosis.

What is claimed is:

1. A periodontological material for modifying the optical properties of cells, the material comprising:
    a basic material; and
    a modification substance distributed in the basic material at a prescribed concentration, wherein the basic material comprises a viscous fluid, a gel, a two-dimensional or three-dimensional porous substrate or a material which hardens in situ;
    wherein the modification substance increases the amount of protoporphyrin formed in a heme cycle; and
    wherein the modification substance comprises either a substrate for enzymes which are active after 5-aminolevulinate synthase up to protoporphyrin synthesis, or an antagonist of the protoporphyrin-degrading ferrochelatase or an iron-inactivating substance.

2. The material according to claim 1, wherein the basic material is inert in relation to the cells.

3. The material according to claim 2 wherein the basic material is inert in relation to a surrounding medium.

4. The material according to claim 1, wherein the basic material is thixotropic.

5. The material according to claim 1, wherein the basic material is a gel and comprises at least one inorganic filler.

6. The material according to claim 1, wherein the basic material is a gel and comprises an organic thickener.

7. The material according to claim 1, wherein the porous substrate provided with the modification substance is in powder form.

8. The material according to claim 1, wherein the basic material is transparent.

9. The material according to claim 1, wherein the film-forming material comprises a surface coating, a resin or a wax.

10. The material according to claim 1, wherein the material additionally contains an active substance.

11. The material according to claim 10 wherein the active substance comprises a fluoride, a disinfectant, a desensitizing substance or an antiadhesive.

12. The material according to claim 1, wherein the material has a pH of from 4.5 to 7.5.

13. The material according to claim 12 wherein the pH of the material is about 5.

14. The material according to claim 1, wherein the basic material comprises a dental impression material.

15. The material according to claim 1, wherein the modification substance is a substance modifying the fluorescence of the cells.

16. The material according to claim 1, wherein the modification substance is a substance modifying the absorption of the cells.

17. The material according to claim 1, wherein the modification substance comprises 5-aminolevulinic acid.

18. The material according to claim 1, wherein the iron inactivating substance comprises an iron complexing agent.

19. The material according to claim 1, wherein the concentration of the modification substance is from 0.5 to 50% by weight.

20. The material according to claim 19 wherein the concentration is between about 5% and 40% by weight.

21. The material according to claim 20 wherein the concentration is between about 10% and 20% by weight.

22. The material according to claim 1 wherein the basic material is a film-forming material.

* * * * *